United States Patent [19]
Snow

[11] Patent Number: 5,863,366
[45] Date of Patent: Jan. 26, 1999

[54] METHOD OF MANUFACTURE OF A CANNULA FOR A MEDICAL DEVICE

[75] Inventor: David W. Snow, Woodside, Calif.

[73] Assignee: Heartport, Inc., Redwood City, Calif.

[21] Appl. No.: 749,683

[22] Filed: Nov. 15, 1996

Related U.S. Application Data

[63] Continuation-in-part of Ser. No. 612,230, Mar. 7, 1996, which is a continuation-in-part of Ser. No. 570,286, Dec. 11, 1995, which is a continuation-in-part of Ser. No. 486,216, Jun. 7, 1995, Pat. No. 5,766,151.

[51] Int. Cl.$^6$ .......................... A61M 25/00; A61M 25/16; B65H 81/00
[52] U.S. Cl. ........................ 156/143; 156/189; 156/192; 156/195; 604/282
[58] Field of Search ........................ 156/195, 143, 156/173, 175, 169, 192, 189, 244.13, 244.26

[56] References Cited

U.S. PATENT DOCUMENTS

| | | | |
|---|---|---|---|
| 243,396 | 6/1881 | Pfarre | 604/282 |
| 3,416,531 | 12/1968 | Edwards | 604/282 |
| 3,671,979 | 6/1972 | Moulopoulos . | |
| 3,769,960 | 11/1973 | Robinson . | |
| 4,000,739 | 1/1977 | Stevens . | |
| 4,056,854 | 11/1977 | Boretos et al. . | |
| 4,122,858 | 10/1978 | Schiff . | |
| 4,173,981 | 11/1979 | Mortensen et al. . | |
| 4,276,874 | 7/1981 | Wolvek et al. . | |
| 4,287,892 | 9/1981 | Schiff . | |
| 4,302,261 | 11/1981 | Simkins | 156/143 X |
| 4,343,672 | 8/1982 | Kanao | 156/195 X |
| 4,527,549 | 7/1985 | Gabbay . | |
| 4,531,936 | 7/1985 | Gordon . | |

(List continued on next page.)

FOREIGN PATENT DOCUMENTS

| | | |
|---|---|---|
| 218275 | 4/1987 | European Pat. Off. . |
| 0 414 50 A1 | 6/1990 | Germany . |
| 0 350 302 | 7/1989 | United Kingdom . |
| WO 91/01689 | 2/1991 | WIPO . |
| WO 91/08791 | 6/1991 | WIPO . |
| 91/17720 | 11/1991 | WIPO . |
| 92/17118 | 10/1992 | WIPO . |
| WO 95/05860 | 3/1995 | WIPO . |

OTHER PUBLICATIONS

Buckberg, G.D. "Strategies and logic of cardioplegic delivery to prevent, avoid, and reverse ischemic and reperfusion damage" *J Thorac Cardio Vase Surg*, 93:127–129 (1987).

Yamaguchi, A., "A case of reoperation using a balloon catheter with blocked pars ascendes aortae" *Kyobu Geka*, 42(11):961–964 (1991).

Peters, W.S. "The promise of cardioscopic surgery" *AustraAs J Cardiac Thorac Surg* 2(3):152–154 (1993).

Rossi, F., "Long–term cardiopulmonary bypass by peripheral cannulation in a model of total heart failure" *J. Thorac Cardio Vasc Surg* 100:914–921 (1990).

Razi, D.M., "The challenge of calcific aortitis" *J. Cardiac Thorac Surg*, 8:102–107 (1993).

Ogawa, K., "Aortic arch reconstruction without aortic cross–clamping using separate extracorporeal circulation" *J. Jpn Assn Thorac Surg*, pp. 2185–2190 (1993).

(List continued on next page.)

*Primary Examiner*—Jeff H. Aftergut
*Attorney, Agent, or Firm*—Jeffrey J. Grainger; Jens E. Hoekendijk

[57] ABSTRACT

An elongate member is coated with a coating, preferably by coextrusion, and the coated elongate member is wound in a helical manner around a mandrel. The coated elongate member preferably has a square cross-sectional shape so that adjacent portions of the coated elongate member engage one another when the coated elongate member is wound around the mandrel. The coated elongate member is then heated so that the coating on adjacent portions of the coated elongate member fuse together to form an integral strcucture. Another layer of material may be provided on the radially inner or outer wall of the coated elongate member.

29 Claims, 11 Drawing Sheets

U.S. PATENT DOCUMENTS

| | | |
|---|---|---|
| 4,540,399 | 9/1985 | Litzie et al. . |
| 4,577,543 | 3/1986 | Wilson . |
| 4,592,340 | 6/1986 | Boyles . |
| 4,601,713 | 7/1986 | Fuqua . |
| 4,664,125 | 5/1987 | Pinto . |
| 4,665,604 | 5/1987 | Dubowik . |
| 4,697,574 | 10/1987 | Karcher et al. . |
| 4,705,507 | 11/1987 | Boyles . |
| 4,741,328 | 5/1988 | Gabbay . |
| 4,764,324 | 8/1988 | Burnham . |
| 4,785,795 | 11/1988 | Singh . |
| 4,804,365 | 2/1989 | Litzie et al. . |
| 4,842,590 | 6/1989 | Tanabe et al. . |
| 4,877,035 | 10/1989 | Bogen et al. . |
| 4,889,137 | 12/1989 | Kolobow . |
| 4,899,787 | 2/1990 | Ouchi et al. . |
| 4,902,272 | 2/1990 | Milder et al. . |
| 4,902,273 | 2/1990 | Choy et al. . |
| 4,943,275 | 7/1990 | Stricker . |
| 4,944,729 | 7/1990 | Buckberg et al. . |
| 5,011,469 | 4/1991 | Buckeberg et al. . |
| 5,015,232 | 5/1991 | Maglinte . |
| 5,024,668 | 6/1991 | Peters et al. . |
| 5,061,257 | 10/1991 | Martinez et al. . |
| 5,069,661 | 12/1991 | Trudell . |
| 5,116,305 | 5/1992 | Milder et al. . |
| 5,163,905 | 11/1992 | Michael . |
| 5,167,628 | 12/1992 | Boyles . |
| 5,171,218 | 12/1992 | Fonger et al. . |
| 5,176,619 | 1/1993 | Segalowitz . |
| 5,176,660 | 1/1993 | Truckai . |
| 5,186,713 | 2/1993 | Raible . |
| 5,190,520 | 3/1993 | Fenton, Jr. et al. . |
| 5,195,942 | 3/1993 | Weil et al. . |
| 5,219,326 | 6/1993 | Hattler . |
| 5,250,038 | 10/1993 | Melker et al. . |
| 5,254,097 | 10/1993 | Schock et al. . |
| 5,270,005 | 12/1993 | Raible . |
| 5,290,230 | 3/1994 | Ainsworth et al. . |
| 5,300,025 | 4/1994 | Wantink . |
| 5,304,132 | 4/1994 | Jang . |
| 5,308,320 | 5/1994 | Safar et al. . |
| 5,312,344 | 5/1994 | Grinfeld et al. . |
| 5,322,509 | 6/1994 | Rickerd . |
| 5,330,433 | 7/1994 | Fonger et al. ............... 604/164 |
| 5,334,142 | 8/1994 | Paradis . |
| 5,334,169 | 8/1994 | Brown et al. . |
| 5,374,245 | 12/1994 | Mahurkar . |
| 5,421,825 | 6/1995 | Farcot . |
| 5,423,745 | 6/1995 | Todd et al. . |
| 5,429,597 | 7/1995 | DeMello et al. . |
| 5,433,700 | 7/1995 | Peters . |
| 5,451,207 | 9/1995 | Yock . |
| 5,464,394 | 11/1995 | Miller et al. . |
| 5,472,435 | 12/1995 | Sutton . |
| 5,478,309 | 12/1995 | Sweezer et al. . |
| 5,538,513 | 7/1996 | Okajima . |
| 5,549,557 | 8/1996 | Steinke et al. . |
| 5,591,142 | 1/1997 | Van Erp . |
| 5,697,905 | 12/1997 | d'Ambrosio . |
| 5,702,373 | 12/1997 | Samson . |

OTHER PUBLICATIONS

Gundry et al. "A comparison of retrograde of cardioplegia versus antegrade cardioplegia in the presence of coronary artery obstruction" *Ann Thorac Surg* 38(2):124–127 (1984).

Lust et al. "Improved protection of chronically inflow–limited myocardium with retrograde coronary sinus cardioplegia" *Circulation III*, 78(5):217–223 (1988).

Crooke et al. "Biventricular distribution of cold blood cardioplegic solution administered by different retrograde techniques" *J Cardiac Thorac Surg.* 102(4):631–636 (1991).

Sabiston, D.C. Textbook of Surgery, 10th Ed. 1972, pp. 2021–2023, 2114–2121.

Ishizaka "Myocardial protection by retrograde cardiac perfusion with cold modified Krebs solution through coronary sinus during complete ischemic arrest for 120 min" *J Jpn Assn Thorac Surg,* 25(12):1592–1601 (1977).

Takahashi, M. "Retrograde coronary sinus perfusion for myocardial protection in aortic valve surgery" *J Jpn Assn Thorac Surg* 30(3):306–318 (1982).

Uchida et al., "Percutaneous cardiomyotomy and valvulotomy with angioscopic guidance" *American Heart Journal* 121(4, part 1):1221–1224 (1991).

Andersen et al., "Transluminal implantation of artificial heart valves . . . " *European Heart Journal,* 13:704–708 (1992).

Uchida et al., "Percutaneous fiberoptic angioscopy of the cardiac valves" *Am Heart J* 121(6, part 1):1791–98 (1991).

"Occlusion Balloon Catheters: Instructions for Use" *Medio-Tech, Boston Scientific Corporation,* Rev. Mar. 1991.

Cosgrove, D.M. "Management of the calcified aorta: An alternative method of occulsion" *Ann Thorac Surg.* 36:718–719 (1983).

Foster and Threlkel "Proximal Control of Aorta with a Balloon Catheter" *Surg. Gynecology & Obstetrics* pp. 693–694 (1971).

Erath and Stoney "Balloon catheter occlusion of the ascending aorta" *Ann Thorac Surg.* 35:560–561 (1983).

Sakaguchi et al. "Aortic valve replacement and coronary artery bypass" *J. Jap Assoc for Thoracic Surg* 41(6):1063–1068 (1993).

Okita, et al. "Utilization of Triple–Lumen Balloon Catheter for Occlusion of the Ascending Aorta During Arotic Arch Surgery with Hypothermic Retrograde Cerebral Circulation Technique Through Left Thoracotomy," *J Card Surg.,* 1995, 10:699–702.

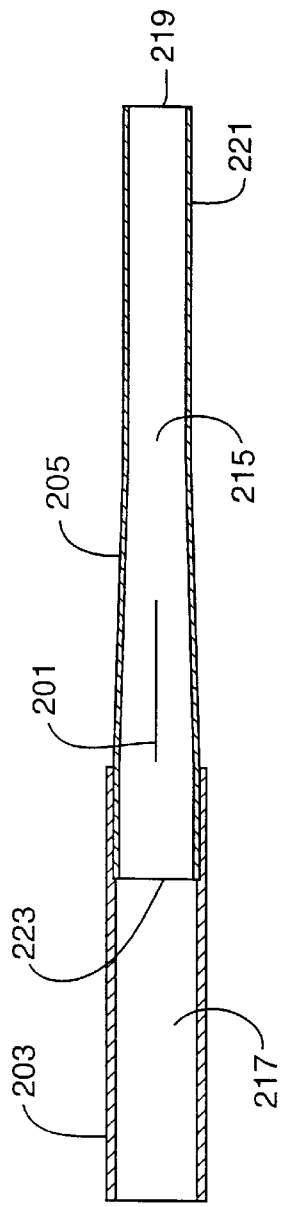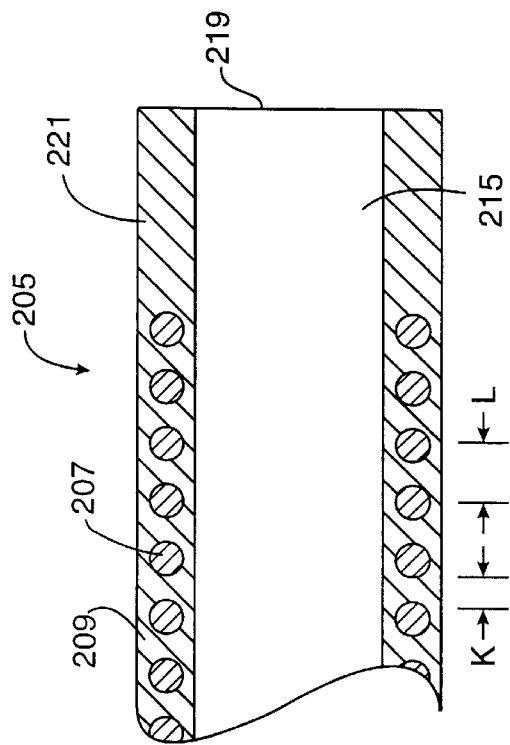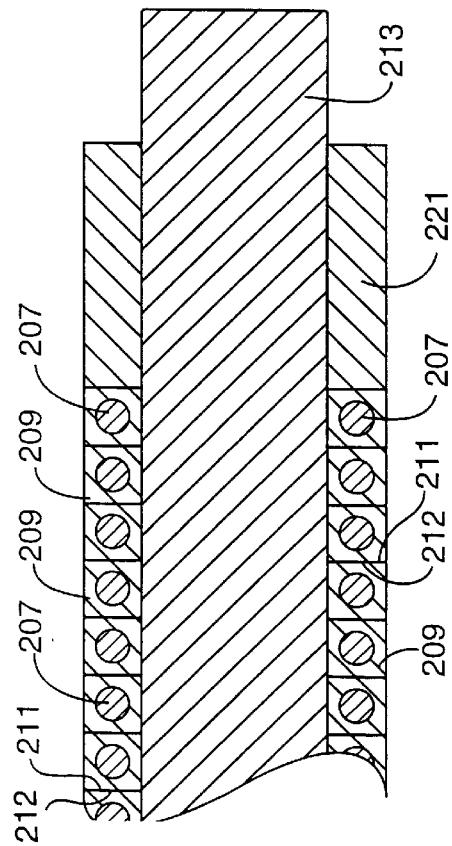

METHOD OF MANUFACTURE OF A CANNULA FOR A MEDICAL DEVICE

CROSS-REFERENCE TO RELATED APPLICATIONS

This application is a continuation-in-part of Ser. No. 08/612,230, filed Mar. 7, 1996 by Snow et al., pending, which is a continuation-in-part of Ser. No. 08/570,286, filed Dec. 11, 1995 by Valley et al., pending, which is a continuation-in-part of Ser. No. 08/486,216, filed Jun. 7, 1995, now U.S. Pat. No. 5,766,151 the complete disclosures of which are incorporated herein by reference for all purposes.

BACKGROUND OF THE INVENTION

The present invention is directed to reinforced hollow tubes and their methods of manufacture and use. A specific application of the present invention is for arterial and venous cardiopulmonary bypass (CPB) cannulas. The present invention is particularly useful as the arterial return cannula for the cardiopulmonary bypass system described in co-pending U.S. patent application Ser. No. 08/282,192 which is incorporated herein by reference. The CPB system has an arterial return cannula which is used to return oxygenated blood to the patient. An aortic occlusion catheter passes through the arterial cannula. The aortic occlusion catheter is used to block blood flow through the ascending aorta and deliver cardioplegic fluid to arrest the heart for performing surgery on the heart and great vessels. The aortic occlusion catheter is inserted through the same lumen in the arterial cannula which is used to return arterial blood to the patient so that the arterial blood essentially passes in the annular space between the aortic occlusion catheter and the arterial return cannula.

An advantage of the CPB system described above is that only one opening in the patient's arterial system is required for both delivery of cardioplegic fluid and return of arterial blood. In order to achieve optimum blood and cardioplegic fluid flow rates, the wall of the arterial cannula must be minimized while retaining enough structural integrity to prevent kinking and/or cracking. The present invention is particularly useful in providing a thin walled cannula which may be used as an arterial return cannula for the system described above.

A known method of making a reinforced cannula is to dip a mandrel in a polymer solution and wrap a metal wire over the polymer. The mandrel is then dipped again to encase the metal wire between two layers of polymer.

Another known method of making a reinforced cannula is to extrude a polymer tubing, wrap a metal wire around the polymer tubing, and extrude another polymer layer over the metal wire.

A problem with the known methods of manufacturing a reinforced cannula is that the spacing between adjacent wires must be relatively large to ensure that the polymer flows between adjacent coils so that the two polymer layers bond together to form an integrated structure. Unfortunately, the relatively large spacing requires a relatively thick polymer layer to provide the necessary strength since the wire has a large pitch. The relatively thick polymer layer is also required to ensure that a sufficient amount of polymer is provided to fill the relatively large space. The resulting cannula has a relatively thick wall.

Thus, a specific object of the present invention is to provide a new method of manufacturing reinforced tubing and, in particular, cannulas for venous withdrawal and arterial return of blood for a cardiopulmonary bypass system.

SUMMARY OF THE INVENTION

The present invention solves the problems associated with prior art cannulas by providing a reinforced, thin-walled cannula and a method of manufacturing the reinforced, thin-walled cannula.

An elongate member, such as a steel or polymer wire, is coated with a coating, preferably a polymer, thereby forming a coated elongate member. A preferred method of coating the material is to coextrude the material over the elongate member. The coated elongate member is then wound helically around a mandrel and heated so that the coating on adjacent parts of the elongate member bond together. The coated elongate member is then mounted to a cannula body.

In a preferred method, the coated elongate member is formed so that opposing sides of the coated elongate member engage one another when the coated elongate member is wrapped around the mandrel. A preferred cross-sectional shape is substantially square. An advantage of the present invention is that the coating does not need to flow between adjacent portions of the helically-wound member since the coated elongate members are configured to have sides which engage one another. In another aspect of the invention, the coated elongate member is compressed after being wound around the mandrel. The coated elongate member is preferably compressed with a heat shrink tube placed over the coated elongate member before heating. The shrink tube compresses the polymer to further ensure bonding between adjacent portions of the coated elongate member.

In another aspect of the present invention, a layer is positioned over and/or below the coated elongate member. The layer is preferably positioned over the coated elongate member and is applied as a tube of material having a larger inner diameter than the largest outer diameter of the coated elongate member. The tube is expanded, preferably by inflating the tube, and the coated elongate member is positioned inside the tube. The tube is then deflated so that it contracts around the coated elongate member. The tube and coated elongate member are then heated to fuse the elongate member and tube together to form an integrated structure. Although it is preferred to apply the layer as a tube, the layer may also be applied by dipping the coated elongated member in a suitable solution.

An advantage of the cannula of the present invention is that the cannula has a thin-walled construction while providing a lumen having a relatively large inner diameter. The lumen is particularly suited to receive an aortic occlusion catheter while still providing enough annular area between the catheter and lumen wall for return of arterial blood to sustain full CPB.

These and other aspects of the invention will become apparent with the following description of the preferred embodiments.

BRIEF DESCRIPTION OF THE DRAWINGS

FIG. 6 is a cross-sectional view of a cannula having a reinforced section coupled to a body.

FIG. 7 is a cross-sectional view of a coated elongate member wrapped around a mandrel.

FIG. 8 is a cross-sectional view of the coated elongate member of FIG. 7 after heating and removal from the mandrel.

DETAILED DESCRIPTION OF THE INVENTION

Figure 1:
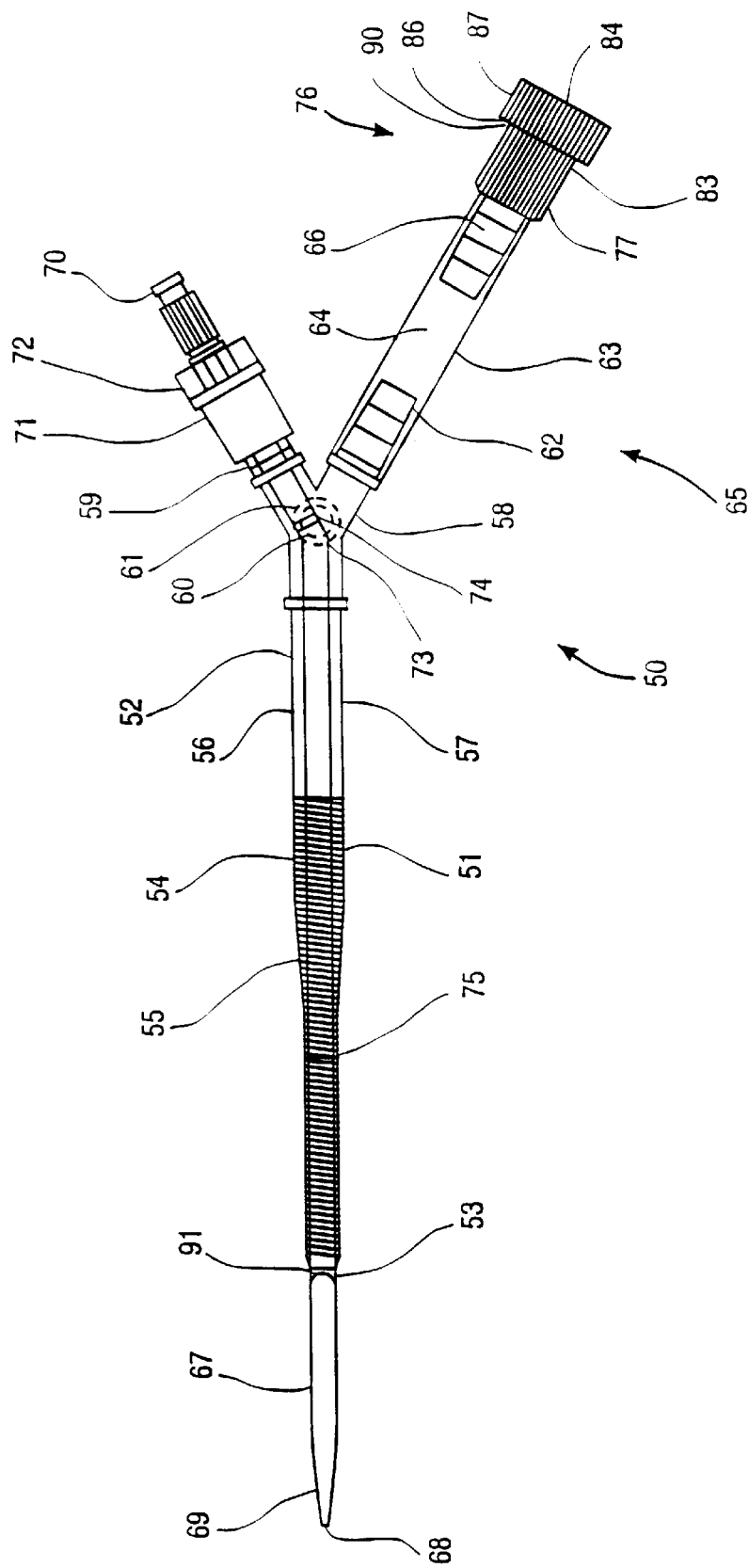
FIG. 1 is a front view of an arterial cannula and introducer sheath for use with an endoaortic occlusion catheter.
Figure 2:
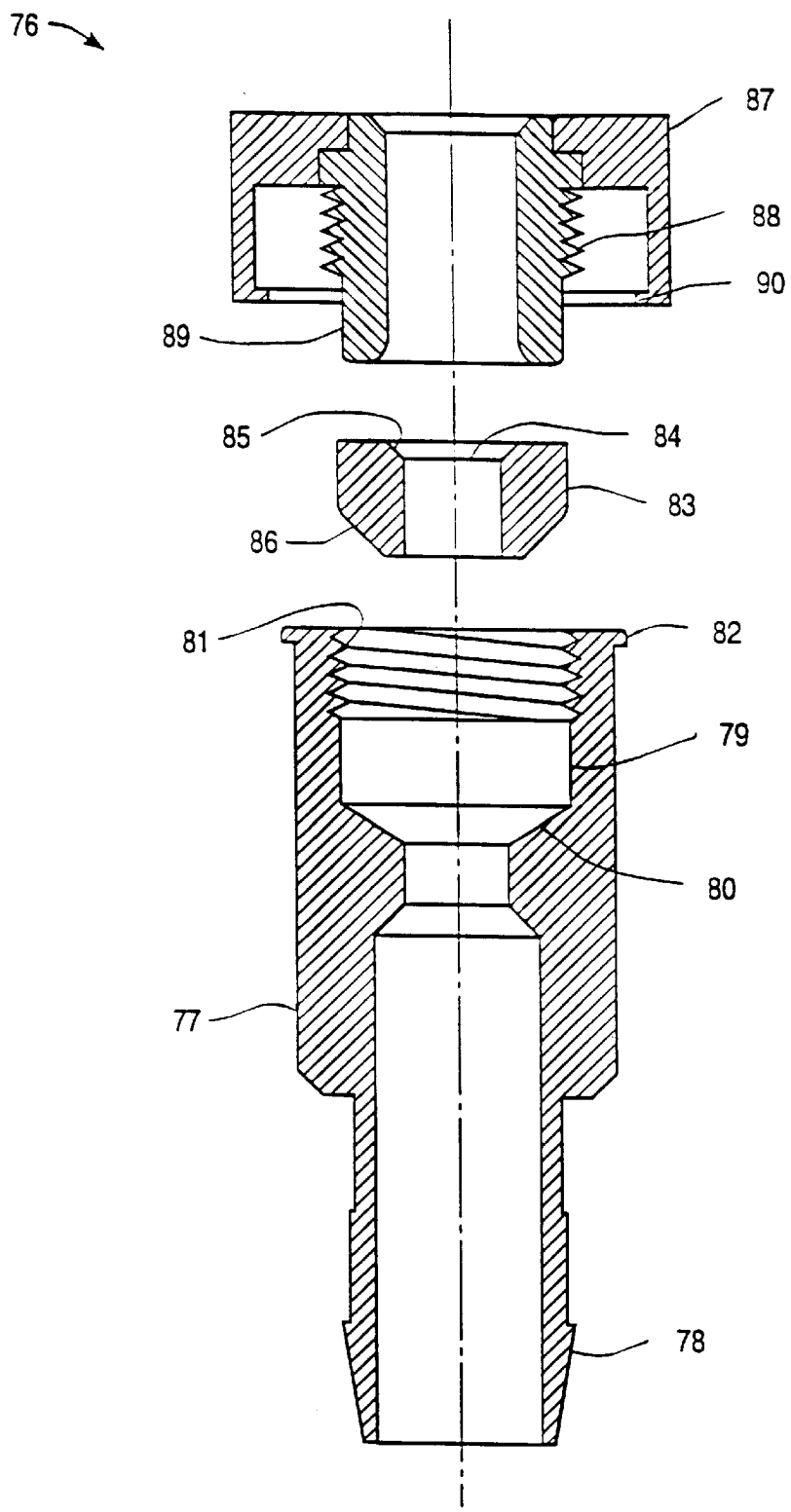
FIG. 2 is a cross sectional view of a hemostasis fitting for the arterial cannula and introducer sheath of FIG. 1.

The invention is directed to cannulas and their methods of manufacture. A particularly useful application of the present invention is for arterial and venous cardiopulmonary bypass cannulas.

Referring to FIGS. 1–4, an endoaortic occlusion catheter 95 is coupled to a cannula 50 that is configured to serve as an arterial bypass cannula and an introducer sheath for introduction of the endoaortic occlusion catheter 95. By configuring the catheter 95 and cannula 50 in this manner, both devices are inserted through the same arterial opening which minimizes trauma to the patient. Use of the cannula 50 to receive an aortic occlusion catheter is merely an example of a use of the present invention and the cannula 50 may be used for any other purpose. Furthermore, the term cannula as used herein refers to any hollow body structure, such as a catheter or trocar, which is inserted into a patient's vascular system. The cannula 50 is coupled to a cardiopulmonary bypass system (not shown) for delivering oxygenated blood to the patient's arterial system. The aortic occlusion catheter 95 has a lumen which is coupled to a source of cardioplegic fluid (not shown). The lumen is coupled to an outlet which is distal to the balloon 96. Cardioplegic fluid is delivered through the lumen and outlet for arresting a patient's heart when the patient is on full cardiopulmonary bypass. The balloon 96 occludes the ascending aorta to prevent oxygenated blood from reaching the coronary arteries and starting the heart prematurely.

The cannula 50 has a body 51 which is preferably made of a transparent, flexible, biocompatible polyurethane elastomer or similar material. In one preferred embodiment, the body 51 has a 45° beveled distal end 53, a proximal end 52, a blood flow lumen 57 extending between the proximal end 52 and the distal end 53, and an outflow port 91 at the distal end 53. Alternatively, the body 51 can have a straight cut distal end with a chamfered or rounded edge. Optionally, a plurality of additional outflow ports may be provided along the length of body 51, particularly near distal end 53. The body 51 is tapered from the proximal end 52 to the distal end 53 and, in one preferred embodiment, the tapered body 51 is reinforced with a coil of flat stainless steel wire 54 embedded in the wall of the body 51. Adjacent to the proximal end 52 of the body 51, proximal to the reinforcing coil 51, is a clamp site 51 which is a flexible section of the body 51 that can be clamped with an external clamp, such as a Vorse type tube occluding clamp, forming a hemostatic seal to temporarily stop blood flow through the lumen 57 of the cannula 50. In a preferred embodiment, the body 51 has a length between about 10 cm and 60 cm, and preferably between about 12 cm and 30 cm. In one particular embodiment, the body 51 has a distal external diameter of approximately 7 mm or 21 French (Charrière scale) and a distal internal diameter of approximately 6.0 mm or 18 French. In a second particular embodiment, the body 51 has a distal external diameter of approximately 7.7 mm or 23 French (Charrière scale) and a distal internal diameter of approximately 6.7 mm or 20 French. Preferably, the proximal end 52 of the body 51 of either embodiment has an internal diameter of approximately ⅜ inch or 9.5 mm. The choice of which embodiment of the cannula 50 to use for a given patient will depend on the size of the patient and the diameter of the artery chosen for the arterial cannulation. Generally, patients with a larger body mass will require a higher infusion rate of oxygenated blood while on cardiopulmonary bypass, therefore the larger arterial bypass cannula 50 should be chosen if the size of the artery allows.

Figure 4:
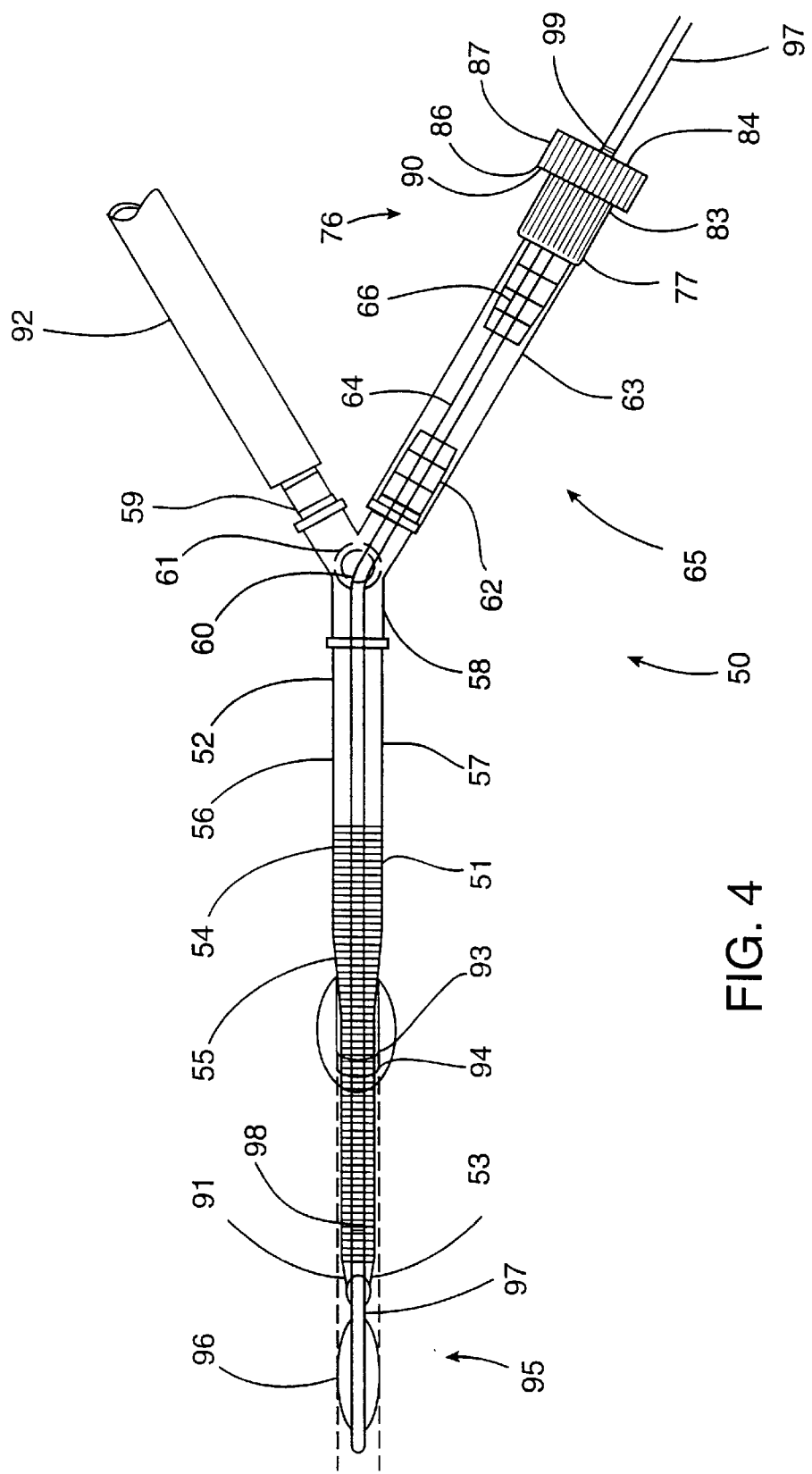
FIG. 4 illustrates the cannula of FIGS. 1 and 2 with the endoaortic occlusion catheter introduced into the patient's femoral artery.

An adapter assembly 65 is connected to the proximal end 52 of the body 51. In one preferred embodiment, the adapter assembly 65 and the body 51 are supplied preassembled as a single, sterile, ready-to-use unit. Alternatively, the adapter assembly 65 can be packaged and sold as a separate unit to be connected to the body 51 at the point of use. The adapter assembly 65 has a Y-fitting 58 which is connected to the proximal end 52 of the cannula body 51. The Y-fitting 58 has a first branch ending in a barbed connector 59 which is configured for fluid connection to tubing 92 from a cardiopulmonary bypass system, as shown in FIG. 4. To prepare the arterial bypass cannula 50 for insertion into a peripheral artery, such as a patient's femoral artery or brachial artery, by an arterial cutdown or by a percutaneous Seldinger technique, a connector plug 71, which is molded of a soft, elastomeric material, is placed over the barbed connector 59. A tapered dilator 67 is passed through a wiper-type hemostasis seal 72 in the connector plug 71. The wiper-type hemostasis seal 72 is a hole through the elastomeric connector plug 71 that has a slight interference fit with the external diameter of the dilator 67. A series of ridges can be molded within the hemostasis seal 72 to reduce the sliding friction on the dilator 67 while maintaining a hemostatic seal. It is understood that any other type of hemostasis seal 72 may be used with the present invention. The dilator 67 has a tapered distal tip 69, a proximal hub 70 with a luer lock connector, and a guidewire lumen 79, sized for an 0.038 inch diameter guidewire, that runs from the distal tip 69 to the proximal hub 70. The diameter of the dilator 67 is such that the dilator 67 substantially fills the cannula lumen 57 at the distal end 53 of the cannula body 51. The length of the dilator 67 is such that the distal tip 69 of the dilator 67 extends approximately 2 to 5 cm, and more preferably 4 to 5 cm, beyond the beveled end 53 of the body 51 when the dilator hub 70 is against the connector plug 70. The dilator 67 may assume a bend 73 in it at the point where the dilator 67 passes through the Y-fitting 58 when the dilator 67 is fully inserted. One or more depth markers 74, 75 can be printed on the dilator 67 with a nontoxic, biocompatible ink. One depth marker 74 may be placed so that, when the marker 74 is just proximal to the hemostasis seal 72 on the elastomeric connector plug 71, the tapered distal tip 69 of the dilator 67 is just emerging from the beveled end 53 of the body 51. In one particular embodiment, the tapered dilator 67 is made of extruded polyurethane with a radiopaque filler so that the position of the dilator can be verified fluoroscopically.

Figure 3:
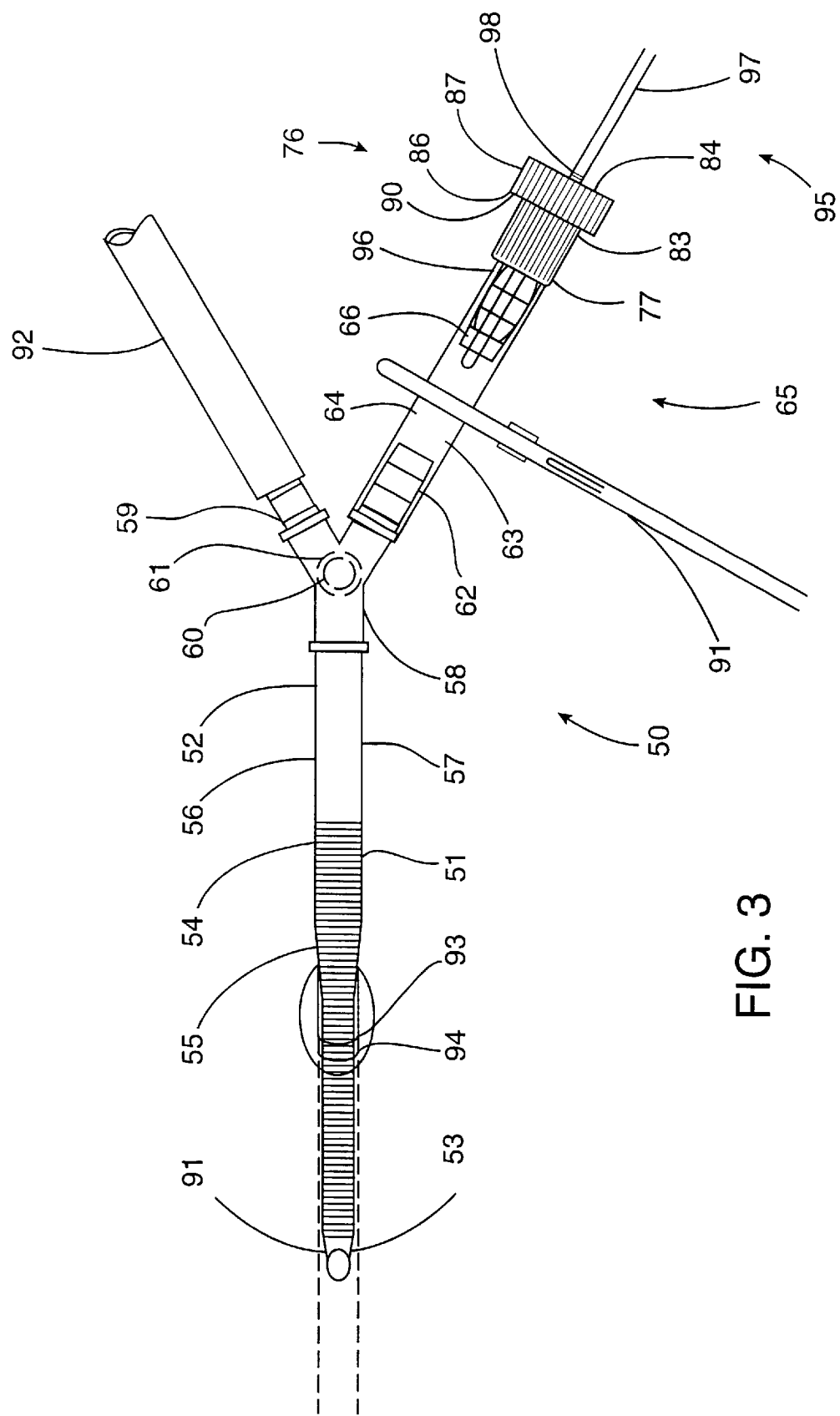
FIG. 3 illustrates the cannula of FIG. 1 with the endoaortic occlusion catheter introduced into the catheter insertion chamber.

A second branch of the Y-fitting 58 is connected to an extension tube 62 which terminates in a hemostasis valve 76 configured to receive the endoaortic occlusion catheter 95 therethrough (FIGS. 3 and 4). The extension tube 62 has a flexible middle section which serves as a proximal clamp site 64 that can be clamped with an external clamp, such as a Vorse type tube occluding clamp, forming a hemostatic seal to temporarily stop blood flow through the lumen 63 of the extension tube 62. The lumen 63 of the extension tube 62 between the proximal clamp site 64 and the hemostasis valve 76 serves as a catheter insertion chamber 66, the function of which will be more fully explained in connection with FIG. 3. The hemostatic seal may, of course, be any other type of seal.

In a preferred embodiment of the arterial bypass cannula 50, the hemostasis valve 76 is a type of compression fitting known in the industry as a Tuohy-Borst adapter, however, any other suitable seal may be used. The adapter 76 is shown in greater detail in FIG. 2. The adapter 76 has a compressible tubular or ring-shaped elastomeric seal 83 that fits within a counterbore 79 in the fitting body 77. The elastomeric seal 83 is preferably made from a soft, resilient, self-lubricating elastomeric material, such as silicone rubber having a hardness of approximately 20–50 and preferably 40–50 Shore A durometer. The elastomeric seal 83 has a central passage 84 with a beveled entry 85 on the proximal end of the passage 84. The elastomeric seal 83 has a beveled distal surface 86 angled at about 45° which fits against a tapered seat 80 in the bottom of the counterbore 79 that is angled at about 60°. A threaded compression cap 87 screws onto the fitting body 77. The threaded cap 87 has a tubular extension 89 which fits within the counterbore 79 in the fitting body 77. An externally threaded section 88 on the proximal end of the tubular extension 87 engages an internally threaded section 81 within the proximal end of the counterbore 79. When the threaded cap 87 is screwed down onto the fitting body 77, the tubular extension 89 bears on the elastomeric seal 83 forcing it against the tapered seat 80 of the counterbore 79. The resultant force on the elastomeric seal 83 squeezes the elastomeric seal 83 inward to close off the passage 84 to make a hemostatic seal. When the threaded cap 87 is unscrewed again from the fitting body 77, the central passage 84 of the elastomeric seal 83 opens up again. The deliberate 15° mismatch between the angle of the beveled distal surface 86 of the elastomeric seal 83 and the tapered seat 80 of the counterbore 79 prevents the elastomeric seal 83 from binding and causes the passage 84 to open up reliably when the threaded cap 87 is unscrewed from the fitting body 87. An internal ridge 90 within the threaded cap 87 engages in a snap fit with an external ridge 82 on the proximal end of the fitting body 77 to keep the threaded cap 87 from being inadvertently separated from the fitting body 77 if the threaded cap 87 is unscrewed to the point where the threads 88, 81 are no longer engaged.

In one particular embodiment, the central passage 84 of the elastomeric seal 83 has an internal diameter of about 5 mm to allow clearance for inserting a catheter 95 with a shaft diameter of 3–4 mm through the adapter 76 without damaging the occlusion balloon 96 mounted on it. The adapter 76 is adjustable through a range of positions, including a fully open position for inserting the balloon catheter 96, a partially closed position for creating a sliding hemostatic seal against the shaft 97 of the catheter 95, and a completely closed position for creating a hemostatic seal with no catheter in the passage 84. In an alternative embodiment, the passage 84 of the elastomeric seal 83 can be sized to have a slight interference fit with the shaft 97 of the catheter 95 when uncompressed. In this embodiment, the adapter 76 has positions which include a fully open position for creating a sliding hemostatic seal against the shaft 97 of the catheter 95, and a completely closed position for creating a hemostatic seal with no catheter in the passage 84. In a second alternative embodiment, a separate ring-like wiper seal (not shown) is added in series with the adapter 76 to create a passive sliding hemostatic seal against the shaft 97 of the catheter 95 without the necessity of tightening the threaded cap 87. Additionally, the adapter 76, in either embodiment, may have a tightly closed position for securing the catheter shaft 97 with respect to the patient. In other alternative embodiments, other known hemostasis valves may be substituted for the Tuohy-Borst adapter 76 as just described.

In a particularly preferred embodiment, the internal surface of the lumen 63 of the extension tube 62 and/or the internal surface of the lumen 57 of the body 51 are coated with a highly lubricious biocompatible coating, such as polyvinyl pyrrolidone, to ease the passage of the endoaortic occlusion catheter 95, and especially the occlusion balloon 96, through these lumens. Other commercially available lubricious biocompatible coatings can also be used, such as Photo-Link™ coating available from BSI Surface Modification Services of Eden Prairie, Minn.; sodium hyaluronate coating available from Biocoat of Fort Washington, Pa.; proprietary silicone coatings available from TUA of Sarasota, Fla.; and fluid silicone or silicon dispersions. Similarly, a distal portion of the exterior of the body 51 can be coated with one of these lubricious biocompatible coatings to facilitate insertion of the arterial bypass cannula 50 into the artery at the cannulation site. Furthermore, the endoaortic occlusion catheter 95 itself, in any of the embodiments described herein, can be coated with one of these lubricious biocompatible coatings to facilitate its insertion and passage through the arterial bypass cannula 50 and the patient's vasculature. Preferably, the occlusion balloon 96 of the endoaortic occlusion catheter 95 should be free of any lubricious coating so that there is sufficient friction between the expanded occlusion balloon and the interior aortic wall to prevent accidental dislodgement or migration of the occlusion balloon 96.

In operation, the arterial bypass cannula 50 is prepared for insertion as shown in FIG. 1, with the tapered dilator 67 in place in the blood flow lumen 57 of the body 51 and with the fitting 76 completely closed. An arterial cutdown is made into an artery, preferably the patient's femoral artery, at the cannulation site or a guidewire is placed percutaneously using the Seldinger technique and the dilator 67 and the distal end 53 of the body 51 are inserted into the lumen of the artery with the bevel up. A suture 94 can be tied around the artery 93 where the body 51, as shown in FIG. 3, inserts to avoid bleeding from the artery 93 at the cannulation site. The dilator 67 is then withdrawn from the body 51, allowing blood to flash back and fill the lumen 57 of the body 51. When the tip 68 of the dilator 67 is proximal to the distal clamp site 56 an external clamp is applied to the distal clamp site 56 to stop further blood flow. The dilator 67 is completely withdrawn and the connector plug 71 is removed so that a tube 92 from the cardiopulmonary bypass system can be attached to the barbed connector 59 of the Y-fitting 58, as shown in FIG. 33. Air is bled from the arterial bypass cannula 50 by elevating the extension tube 62 and opening the fitting 76 slightly and releasing the external on the distal clamp site 56 to allow the blood to flow out through the fitting 76. Alternatively, air can be bled out of the arterial bypass cannula 50, through an optional vent fitting with a luer cap (not shown) that can be provided on the Y-fitting 58 or an infusion line and a three-way stopcock. The optional vent fitting can be also used as a port for monitoring perfusion pressure within the arterial bypass cannula 50. Once the air is bled out of the system, the external clamp can be removed from the distal clamp site 56 the cardiopulmonary bypass system pump can be turned on to perfuse the patient's arterial system with oxygenated blood at a rate of about 3 to 6 liters/minute, preferably at a pump pressure of less than about 500 mm Hg.

To introduce the endoaortic occlusion catheter 95 into the arterial bypass cannula 50, an external clamp 91 is placed on the proximal clamp site 64, as shown in FIG. 3, to stop blood from flowing out through the extension tube 62 and the adapter 76 is opened all the way by unscrewing the threaded cap 87 to open up the passage 84 through the elastomeric seal 83. The distal end of the endoaortic occlusion catheter 95 with the occlusion balloon 96 mounted thereon is inserted through the passage 84 of the adapter 76 into the insertion chamber 66 of the arterial bypass cannula 50. Optionally, first and second depth markers 98, 99 may be printed on the shaft 97 of the endoaortic occlusion catheter 95 with a nontoxic, biocompatible ink. The first depth marker 98 on the catheter 95 indicates when the occlusion balloon 96 is entirely distal to the elastomeric seal 83. When the first depth marker 98 is positioned just proximal to the threaded cap 87, the adapter 76 should be tightened to create a sliding, hemostatic seal around the catheter shaft 97. Now, the clamp 91 can be removed to allow the catheter 95 to be advanced distally through the arterial bypass cannula 50.

Before the endoaortic occlusion catheter 95 enters the blood flow lumen 57 within the Y-fitting 58, the perfusion rate from the cardiopulmonary bypass system pump should be temporarily turned down to a rate of about 1 to 2 liters/minute to avoid hemolysis, tubing disruptions or other complications due to the additional flow resistance caused by the occlusion balloon 96 as it passes through the blood flow lumen 57. The catheter 95 can now be advanced distally until the occlusion balloon 96 is distal to the distal end 53 of the body 51. A second depth marker 99 on the catheter 95 indicates when the occlusion balloon 96 is entirely distal to the distal end 53 of the body 51. When the second depth marker 98 reaches the proximal end of the threaded cap 87, as shown in FIG. 3, the perfusion rate from the cardiopulmonary bypass system pump should be returned to a rate of about 3 to 6 liters/minute. The endoaortic occlusion catheter 95 can now be advanced into the ascending aorta for partitioning the heart and inducing cardioplegic arrest according to the methods described above. When the endoaortic occlusion catheter 95 is in position within the ascending aorta the adapter 76 can be tightened around the catheter 95 to act as a friction lock to hold the catheter in place.

After completion of the surgical procedure on the heart, the endoaortic occlusion catheter 95 can be removed from the cannula 50 by reversing the sequence of operations described above. The cannula 50 can remain in place until the patient has been weaned from cardiopulmonary bypass, then the cannula 50 can be removed and the arterial puncture site repaired.

It should be noted that for the venous side of the cardiopulmonary bypass system, a similar dual purpose venous bypass cannula and introducer sheath with the above-described features can be used for accessing the femoral vein and for introducing a venting catheter or other devices into the venous side of the circulatory system. In a venous configuration the dual purpose venous bypass cannula and introducer sheath preferably has an external diameter of about 21 to 32 French units, an internal diameter of about 18 to 30 French units, and a length of about 50 to 75 cm.

Figure 5:
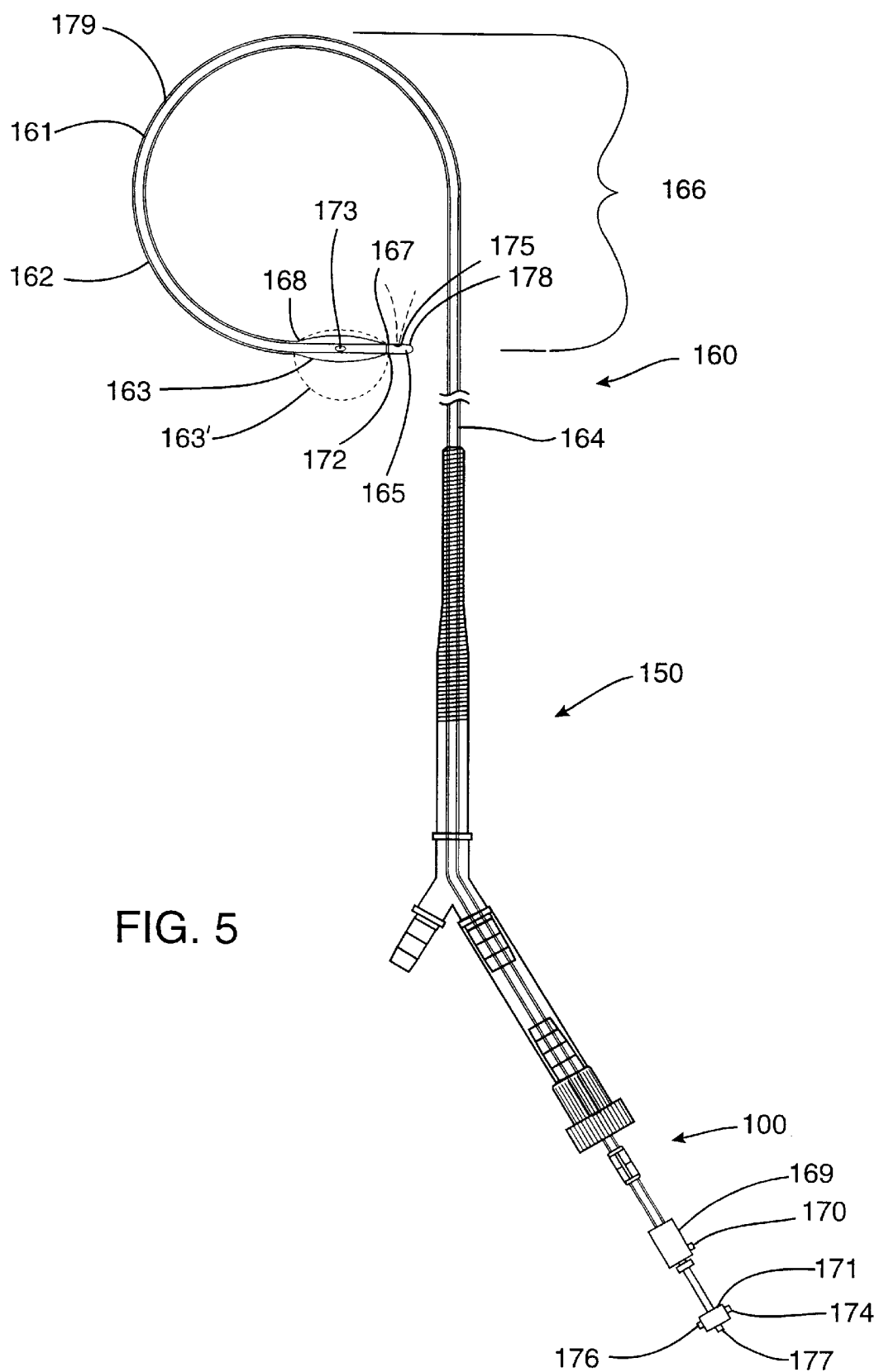
FIG. 5 illustrates a multifunction embodiment of the endoaortic occlusion catheter combined with the arterial cannula and introducer sheath.

It should be noted that while several aspects of the present invention have been illustrated and discussed separately in the foregoing description, many of these aspects can be advantageously combined into a single, multifunction embodiment. As an illustrative example, FIG. 5 shows a multifunction embodiment of the endoaortic occlusion catheter 160 combining several of the inventive aspects previously discussed. As discussed above, however, any other aortic occlusion catheter may be used and preferred aortic occlusion catheters are described in U.S. patent application Ser. No. 08/692,992. The shaft 164 of the catheter 160 has a coaxial construction with an inner 161 and outer 162 tubular member. The shaft 164 may be made with varying degrees of stiffness along the length of the shaft 164, culminating in a soft atraumatic tip 165 which may be highly loaded with a radiopaque filler. The shaft 164 may be made with a precurved distal portion 166 or with a precurved distal portion 166 which is out of plane with the proximal portion of the shaft 164. An expandable occlusion balloon 163 is mounted on the distal portion 166 of the shaft 164. The balloon 163 preferably has a low profile deflated state with an ellipsoidal shape. In addition, the balloon 163 may have an eccentric or asymmetrical inflated profile 163' which would also provide a steering means for the distal tip of the catheter.

The occlusion balloon 163 is mounted with its distal balloon neck 167 attached to the inner tubular member 161 and its proximal balloon neck attached to the outer tubular member 162. The inner tubular member 161 is attached at its proximal end to a first hub 171 and the outer tubular member 162 is attached at its proximal end to a second 169 hub 171 which are axially slidably and/or rotatable with respect to one another. An infusion fitting 177, such as a luer lock, on the first hub 171 is connected to an infusion lumen 178 which terminates at the distal end of the catheter 160. An inflation fitting 170, preferably a luer lock, on the second hub 171 is connected to an inflation lumen 179 defined by an annular space between the inner 161 and outer 162 tubular members which communicates with the interior of the occlusion balloon 163.

The second hub 169 may be moved proximal and/or rotated with respect to the first hub 171 to minimize the deflated profile of the occlusion balloon 163. The lower deflated profile of the occlusion balloon 163 facilitates easy insertion of the catheter 160 through a dual function arterial cannula and introducer sheath 50. When the endoaortic occlusion catheter 160 is combined with the dual function arterial cannula and introducer sheath 50, the shaft 164 of the catheter 160 should be made with an additional 20–25 cm of length for a total shaft length of approximately 100–115 cm. The diameter of the catheter shaft 164 should also be minimized as much as possible to reduce the amount of cross sectional area the catheter shaft 164 takes up in the blood flow lumen of the arterial cannula 50. To this end, this combined embodiment is made with a distal pressure transducer 172 and a balloon pressure monitoring transducer 173 mounted on the inner tubular member 161. The distal pressure transducer 172 and the balloon pressure monitoring transducer 173 are electrically connected to an electrical connector 174 on the first hub 171. Also on the first hub 171 is a fiberoptic connector 176 which connects to a fiberoptic bundle 175 which terminates with a means for directing a lateral beam of light at the distal end of the catheter 160 for aortic transillumination and/or for facilitating nonfluoroscopic placement of the catheter 160. The fiberoptic bundle 175 may also be made as a separate unit for insertion through the infusion lumen 178 of the catheter 160 to further reduce the catheter shaft diameter while maintaining maximum functionality. The diameter of the catheter shaft 164 can thus be reduced to as small as 8 to 10.5 French (2.7–3.5 mm diameter).

Referring to FIG. 6, a cross-sectional view of another preferred cannula 201 is shown. A specific application of the present invention is for arterial and venous cannulas for a cardiopulmonary bypass system. The methods and devices described herein in connection with arresting a patient's heart and placing the patient on cardiopulmonary bypass are incorporated here for use with the cannula 201 described below and any other cannula described herein. The cannula 201 includes a body 203 and a reinforced section 205. As will be discussed in greater detail below, the reinforced section 205 has a thin wall which maximizes the lumen size for a given outer diameter.

Referring to FIG. 7, an apparatus for forming the reinforced section 205 is shown. The reinforced section 205 of the cannula 201 is preferably manufactured with an elongate member 207 coated with a coating 209. The elongate member 207 may be made of any suitable material which has the requisite structural characteristics such as stainless steel, nickel titanium, or a polymer. A preferred material is 304V stainless steel wire having a 0.008 inch diameter. The elongate member 207 may have any cross-sectional shape and a preferred shape is circular.

The elongate member 207 is preferably coated with the coating 209 by coextruding the elongate member and the coating 209. Any suitable coating 209 may be used and preferred coatings include polymers and specifically polyurethane, PVC, polyether block amide which can be purchased from Elf Atochem Inc. under the name PEBAX, and styrene block copolymer which can be purchased from Shell under the name KRATON. A preferred polyurethane is polytetramethylene glycol ether which can be purchased from Dow under the name Dow 2363 PELLETHANE 80AE.

The coating 209 is extruded over the elongate member 207 so that the coating 209 has opposing sides 211, 212 which are configured to engage one another when the coated elongate member 207 is wrapped around a mandrel 213. A preferred shape is a quadrangle, and specifically a square, however, any other shape may be used including irregular shapes so long as the opposing sides 211, 212 are configured to engage one another. The square cross-sectional shape preferably has sides having lengths between 0.010 and 0.020 inch and more preferably between 0.010 and 0.015 inch and most preferably 0.014 inch. The relative dimensions for the thickness of the cannula has been exaggerated as compared to the inner diameter for clarity with the actual dimensions being provided herein.

The coated elongate member 207 is wrapped around the mandrel 213 in a helical shape. The mandrel 213 is preferably coated with a lubricious coating such as TFE to prevent sticking. An advantage of the present invention over other methods of forming a cannula is that the coating 209 encasing the reinforcing member 207 does not have to flow between adjacent portions of the elongate member 207 since the elongate member 207 is coextruded to have a shape in which the opposing sides 211, 212 already engage one another. A shrink tube (not shown), preferably a heat shrink tube such as a polyester or fluorinated ethylene propylene (FEP) tube, may also be positioned around the elongate member 207 to facilitate bonding. The shrink tube is preferably removed after heating. The wound coated elongate member 207 may also be dipped in a polymer solution such as polyurethane and tetrahydrofuran (solvent) to enhance the structural characteristics of the reinforced section 205. Furthermore, the coating or tube may also be applied over the wound coated elongate member. Alternatively, a tube may be positioned over the mandrel 213 and the coated elongate member 207 may be wound over the tube. The reinforced section 205 may be made of more than one layer of the coated elongate member 207 and the coated elongate member 207 may be wrapped in different directions to increase the hoop and tensile strength. Although it is preferred that the elongate member 207 has a constant cross-sectional profile, the elongate member 207 may also have differing sizes to provide stiff and flexible areas.

After the coated elongate member 207 has been wrapped around the mandrel 213, the coated elongate member 207 is heated to melt the coating 209 and fuse adjacent portions of the coating 209 together to form an integrated structure. The coated elongate member 207 is preferably heated using an oven, however, any other heating method may be used including an IR lamp, heating the mandrel 213, or a combination thereof. The coated elongate member 207 is then cooled and removed from the mandrel 213 thereby forming the reinforced section 205 of the cannula 201.

Referring to FIG. 8, the resulting reinforced section 205 is shown. The coating 209 on the elongate member 207 fuses together so that the coating 209 forms a matrix which is reinforced by the elongate member 207. Although it is preferred to heat the coated elongate member 207 to fuse the material together, the coated elongate member may also be coated with a solvent before winding the coated elongate member around the mandrel. The solvent would fuse the adjacent material together and would flash off leaving the fused material.

Referring again to the cross-section of FIG. 6, the reinforced section 205 has a lumen 215 therethrough for delivering or withdrawing fluids from a patient. The reinforced section 205 is attached to the body 203 by any method and is preferably bonded to the body 203 by insert molding. The body 203 includes a lumen 217 which is fluidly coupled to the lumen 215 of the reinforced section 205. The body 203 has been simplified and may include valves, a Y-connection, luer connections or any other features. Furthermore, the body 203 is preferably configured to engage a ⅜ inch fitting which is a standard size for cardiopulmonary bypass systems. The lumen 215 of the reinforced section 205 may be any size but preferably has an internal diameter of at least 0.180 and more preferably at least 0.236 and most preferably at least 0.242 but no more than 0.375 inch.

A distal end 219 of the cannula 201 has an atraumatic tip 221 for introduction into the patient. The atraumatic tip 221 is preferably an integral extension of the coating 209 (see FIG. 8) extending beyond the reinforced section 205. The atraumatic tip 221 has a length of at least 0.050 and a thickness adjacent to the reinforced section which is preferably the same as the reinforced section.

A proximal end 223 of the reinforced section 205 is flared outward slightly so that the proximal end 223 has a larger lumen than the distal end 219. The proximal end 223 preferably forms an angle of between 2° and 10° and more preferably between 4° and 6° with respect to a longitudinal axis of the cannula 201.

The cannula 201 is particularly useful for arterial return and venous drainage cannulas for the cardiopulmonary bypass system described above since the cannula 201 can be manufactured with a thin wall. As such, the reinforced section 205 preferably has a thickness between 0.010 and 0.025 inch and more preferably between 0.013 and 0.020 inch and most preferably between 0.014 and 0.017 inch. The preferred thickness provides the necessary structural characteristics while maximizing the lumen size so that flow rates through the cannula are optimized. The cannula 201 of the present invention also has a unique spacing between adjacent portions of the coated elongate member. Referring to FIG. 8, a gap K between adjacent portions of the elongate member 207 is preferably less than 0.019 inch and more preferably less than 0.006 inch and most preferably less than 0.004 inch. A centerline spacing L between adjacent portions of the elongate member 207 is preferably less than 0.022 inch and more preferably less than 0.018 inch and most preferably less than 0.014 inch.

Figure 9:
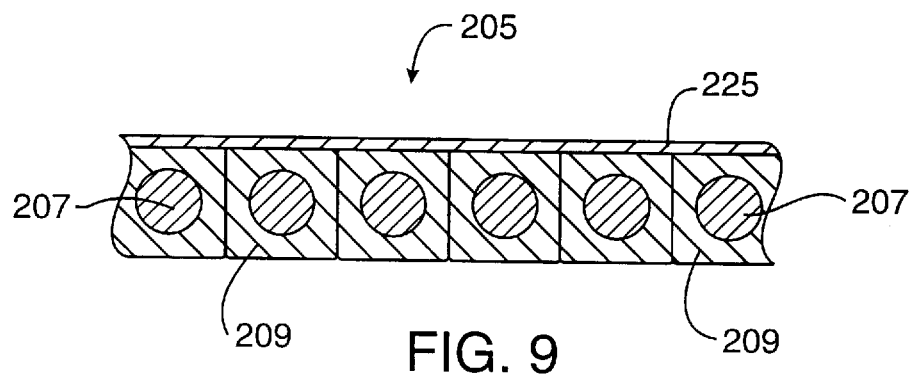
FIG. 9 is a cross-sectional view of a second construction for the reinforced section.

Referring to FIG. 9, a second preferred construction is shown for the reinforced section 205. The elongate member 207 and coating 209 are preferably the same as described above in connection with FIGS. 7–8, however, another layer 225 is positioned either over the elongate member 207 or below the elongate member 207 to increase the strength of the reinforced section 205. When the layer 225 is on the radially inner wall of the cannula 201, the layer 225 may be applied by dipping the mandrel 213 in a suitable solution, extruding the layer over the mandrel 213 or positioning a tube over the mandrel 213. The coated elongate member 207 is then wrapped around the mandrel 213 and heated to fuse the coating 209 and layer 225 together. When the layer 225 is on the radially outer wall of the cannula, the layer 225 may be applied by dipping the coated elongate member 207 in a suitable solution after wrapping the coated elongate member 207 around the mandrel 213, extruding the layer 225 over the coated elongate member 207 wound around the mandrel 213, or positioning a tube over the coated elongate member wound around the mandrel 213 and fusing it to the coated elongate member. The coated elongate member 207 and coating 209 have the same preferred dimensions described above. The layer 225 has thickness of no more than 0.007 inch and more preferably between 0.001 and 0.003 inch and is preferably made of the same materials as the coating 209 described above. FIG. 9 depicts the reinforced section 205 before heating, however, after heating the polymer layer 225 and coating 209 fuse together to form an integrated structure.

Figure 10:
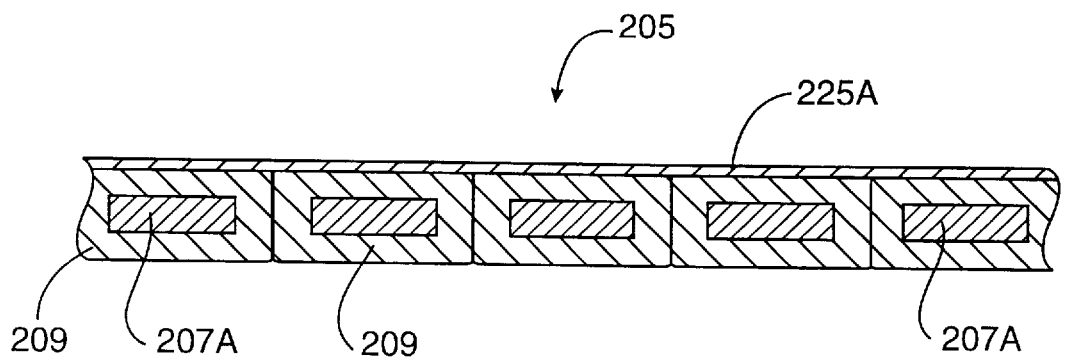
FIG. 10 is a cross-sectional view of a third construction for the reinforced section.

Referring to FIG. 10, a third preferred construction for the reinforced section 205 is shown. The reinforced section 205 is made according to the same procedure described above except that a different elongate member 207A is used. The elongate member 207A is preferably made of metal and has a quadrangle shaped cross-section. A preferred elongate member is a stainless steel flat wire having cross-sectional dimensions of 0.005 inch by 0.020 inch. The elongate member 207A is preferably coextruded with the coating 209 to a thickness of 0.003 all around although any thickness may be used. A layer 225A, which is preferably the same as the layer 225 described above, may be positioned on the radially inner or outer wall of the cannula. The resulting structure yields an inner diameter of at least 0.180 inch, more preferably at least 0.236 inch, and most preferably at least 0.242 inch and no more than 0..375 inch. The resulting reinforced section 205 has a thickness of 0.011 inch without the layer 225A and 0.013 inch with the layer 225A. The reinforced section 205 may also be formed without the layer 225A so that the wall thickness of the cannula is minimized. FIG. 10 depicts the reinforced section 205 before heating, however, after heating the layer 225A and coating 209 fuse together to form an integrated structure.

Figure 11:
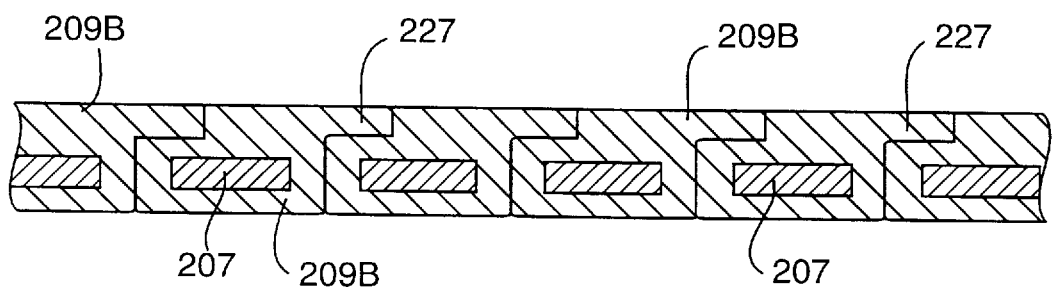
FIG. 11 is a cross-sectional view of a fourth construction for the reinforced section.

Referring to FIG. 11, a fourth preferred construction for the reinforced section 205 is shown. The reinforced section 205 is made according to the same procedure described above and has the same elongate member 207 as described in connection with FIG. 70. The coating 209B has an overlapping portion 227 which lies over an adjacent portion of the coated elongate member 207B. The elongate member 207B is a 0.005 inch by 0.020 inch stainless steel flat wire, and the coating has a width of 0.003 inch all around the elongate member 207. The overlapping portion 227 has a thickness of 0.005 inch and a length of 0.013 inch. The overlapping portion 227 provides an interlocking relationship between adjacent portions of the coated elongate member 207. FIG. 11 depicts the reinforced section 205 before heating, however, after heating the material from adjacent portions of the coating 209 and the overlapping portion 227 fuse together to form an integrated structure.

Figure 12:
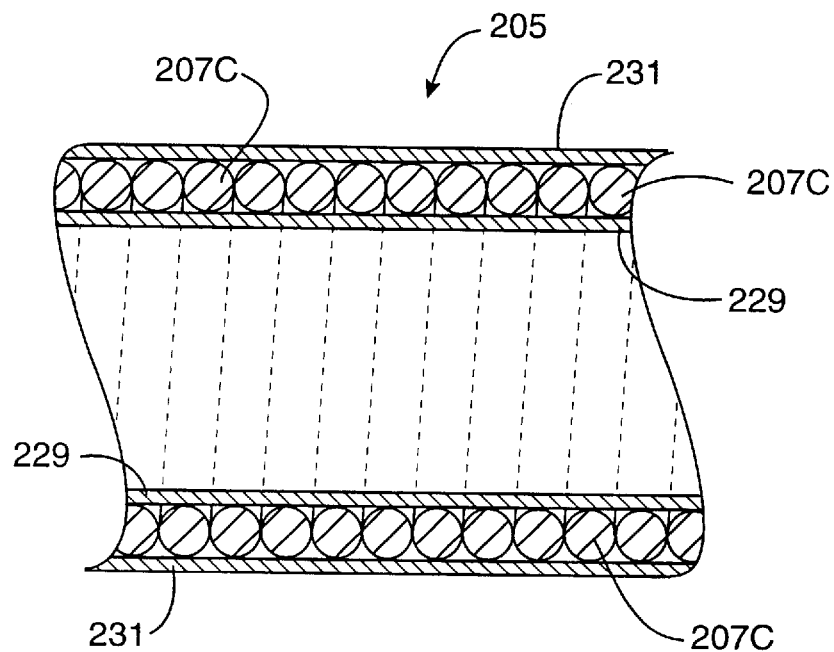
FIG. 12 is a cross-sectional view of a fifth construction for the reinforced section.

Referring to FIG. 12, a fifth preferred construction for the reinforced section 205 is shown. The fifth preferred construction differs from the first through fourth preferred constructions in that the elongate member 207C is not coated before being wrapped around the mandrel. As discussed above, a known method of manufacturing reinforced tubing is to extrude a tube, mount the tube on a mandrel, wind a metal coil around the tube and position another tube over the coil. The tubes and coil are then heated so that the inner and outer tubes bond together. A problem with the known method is that relatively thick walled tubes are formed since the layers must be relatively thick to ensure sufficient strength since the wire must be spaced apart.

The elongate member 207C of FIG. 12 is made of a polymer, preferably 75D polyurethane, so that radially inner and outer polymer layers 229, 231 can fuse to the elongate member 207C to form an integrated structure. Thus, the polymer layers 229, 231 do not need to fuse together completely to form an integrated structure which overcomes a problem with prior art methods of forming reinforced cannulas. The polymer layers 229, 231, preferably 80A polyurethane, are positioned on opposite sides of the polymer elongate member 207C. The polymer layers 229, 231 are preferably softer than the polymer used for making the elongate member 207C. The elongate member 207C preferably has a diameter between 0.005–0.020 inch and more preferably between 0.008 and 0.012 inch. The layers 229, 231 preferably have a thickness of 0.002 to 0.015 inch and more preferably 0.005 to 0.10 inch. The elongate member 207C is preferably wound so that adjacent portions of the elongate member 207C contact one another, however, the polymer elongate member 207C may be wound so that a space exists between adjacent portions of the elongate member 207C. Furthermore, although the elongate member 207C preferably has a circular cross-sectional shape the elongate member 207C may have any other shape. The polymer layers 229,231 may be applied in any manner including coextrusion, dipping or by simply using preformed tubes.

The polymer layers 229, 231 are preferably heated so that they bond with the elongate member 207C. The polymer layers 229, 231 are preferably positioned on both sides of the elongate member 207C before heating the layers 229, 231, however, the layers 229, 231 may also be applied one at a time. By constructing the reinforced section 205 in this manner, the polymer does not need to flow completely between each part of the elongate member 207C to provide an integrated structure since the layers 229, 231 must simply bond to the elongate member 207C rather than having to bond with the opposing layer 229, 231. FIG. 12 depicts the reinforced section 205 before heating, however, after heating the polymer material from the layer 225A and coating 209 fuse together to form an integrated structure.

Figure 13:
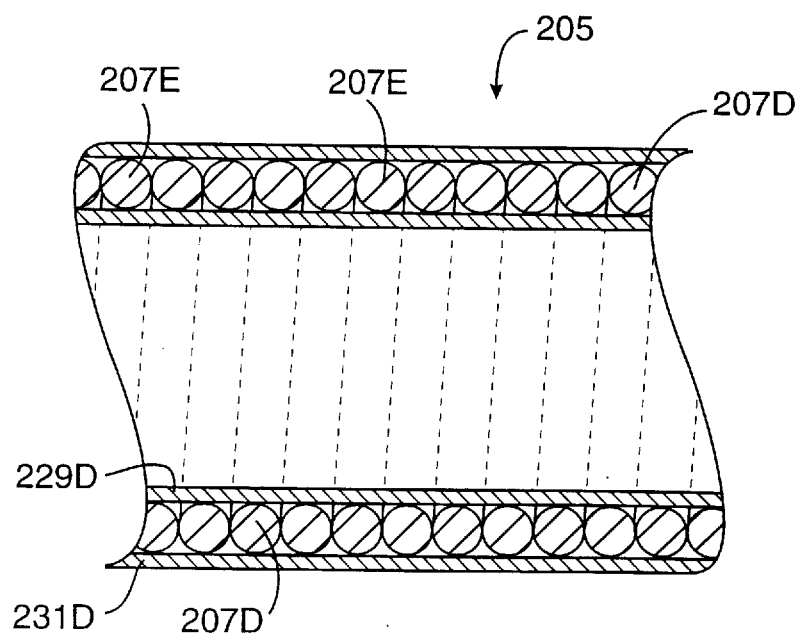
FIG. 13 is a cross-sectional view of a sixth construction for the reinforced section.

Referring to FIG. 13, a sixth preferred construction for the reinforced section 205 is shown with polymer and metal elongate members 207D, 207E wound together. Two polymer layers 229D, 231D are positioned on opposite sides of the elongate members 207D, 207E and may be provided in any manner described above. The polymer layers 229D, 231D are preferably softer than the polymer elongate member 207D. A preferred material for the polymer layers 229D, 231D is 75D polyurethane and a preferred material for the polymer elongate member 207D is 80A polyurethane. The soft polymer layers 229D, 231D are melted to bond to the polymer elongate member 207D thereby forming an integrated structure. The metal elongate member 207E provides structural strength and is preferably a stainless steel wire although any metal may be used. Although it is preferred that the elongate members 207D, 207E have circular cross-sectional shapes, the elongate members may have any other shape. Furthermore, although it is preferred that the elongate members have the same cross-sectional shape, the elongate members may also have different cross-sectional shapes. FIG. 13 depicts the reinforced section 205 before heating, however, after heating the material from the layers 229D, 231D and the elongate member 207D will fuse together to form an integrated structure.

Figure 14:
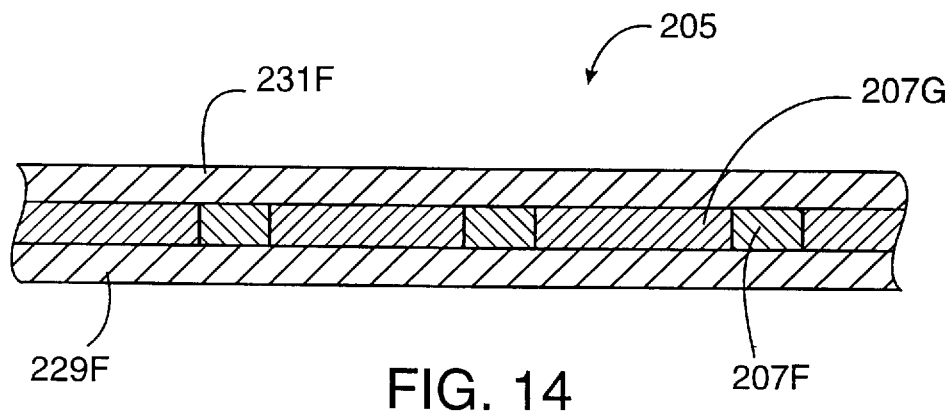
FIG. 14 is a cross-sectional view of a seventh construction for the reinforced section.

Referring to FIG. 14, a seventh preferred construction for the reinforced section 205 is shown. A polymer elongate member 207F is wound together with a flat elongate member 207G. The polymer material for the polymer elongate member 207F may be any polymer and is preferably 75D polyurethane. The flat elongate member 207G is preferably the same as the elongate member 207A described above in connection with FIG. 10. Two layers of polymer 229F, 231F encase the polymer and flat wire elongate members 207F, 207G. The polymer layers 229F, 231F are preferably softer than the polymer material of the elongate member 207F. The polymer layers 229F, 231F are preferably 80A polyurethane, however, any polymer may be used. The polymer layers 229F, 231F may be applied in any manner described above. The polymer layers 229F, 231F preferably have a thickness between 0.002 and 0.010 inch and more preferably between 0.004 and 0.008 inch. The polymer layers 229F, 231F are heated to bond to the polymer elongate member 207. FIG. 13 depicts the reinforced section 205 before heating, however, after heating the layers 229F, 231F and elongate member 207F fuse together to form an integrated structure.

Figure 15:
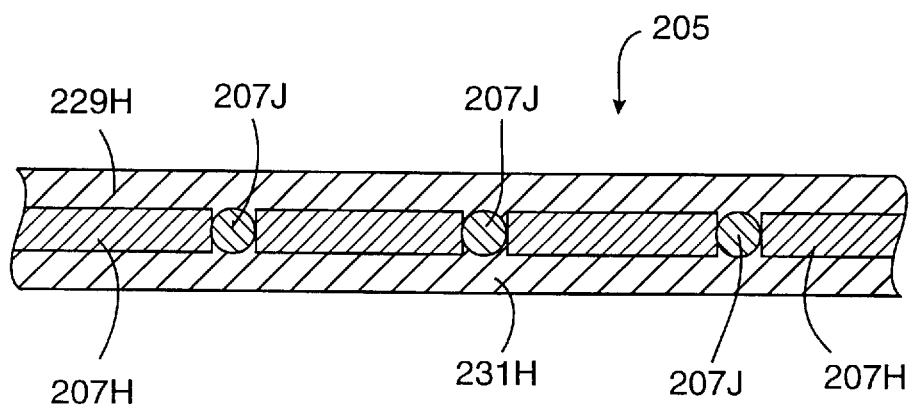
FIG. 15 is a cross-sectional view of a eighth construction for the reinforced section.

Referring to FIG. 15, an eighth preferred construction for the reinforced section 205 is shown. A first elongate member 207H is preferably the same as the elongate member 207A described above in connection with FIG. 10. A second elongate member 207J is made of a polymer and has a thickness between 0.003 and 0.008 inch and more preferably 0.005 inch. Two polymer layers 229H, 231H encase the elongate members. The layers 229H, 231H are preferably 80A polyurethane having a thickness between 0.002 and 0.010 inch and more preferably between 0.004 and 0.008 inch. The polymer layers 229H, 231H may be applied in any manner described above. The polymer layers 229H, 231H are heated to bond to the second elongate member 207J.

Figure 16:
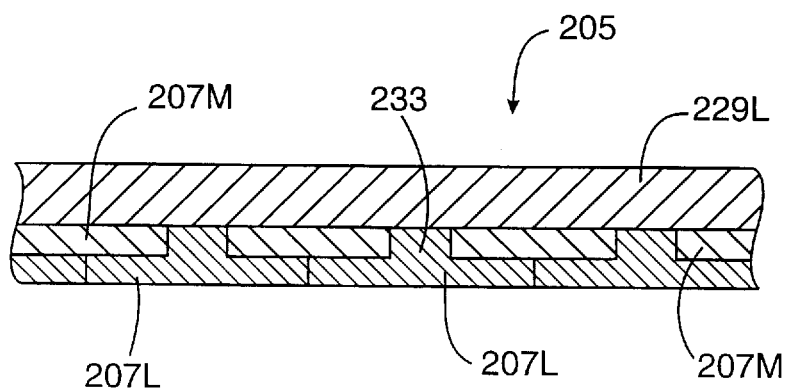
FIG. 16 is a cross-sectional view of a ninth construction for the reinforced section.

Referring to FIG. 16, a ninth preferred construction for the reinforced section 205 is shown. A first elongate member 207L is wound around a mandrel 213 (not shown). The first elongate member 207L is preferably made of polymer, preferably 80A polyurethane, and has a T-shaped cross-sectional shape. The T-shaped cross-sectional shape has a width of 0.028 inch and a height of 0.008 inch. The first elongate member 207L has a radial extension 233 having a width of 0.008 inch. A second elongate member 207M, which is preferably the same as the elongate member 207A described above in connection with FIGS. 70, is wound over the first elongate member 207L. A polymer layer 229L is then positioned over the first and second elongate members 207L, 207M and is preferably 80A polyurethane having a thickness of 0.008 inch. The polymer layer 229L may be applied in any manner described above. The polymer layer 229L is then heated so that the polymer layer 229L and the radial extension 233 bond to one another to form an integrated structure.

Figure 17:
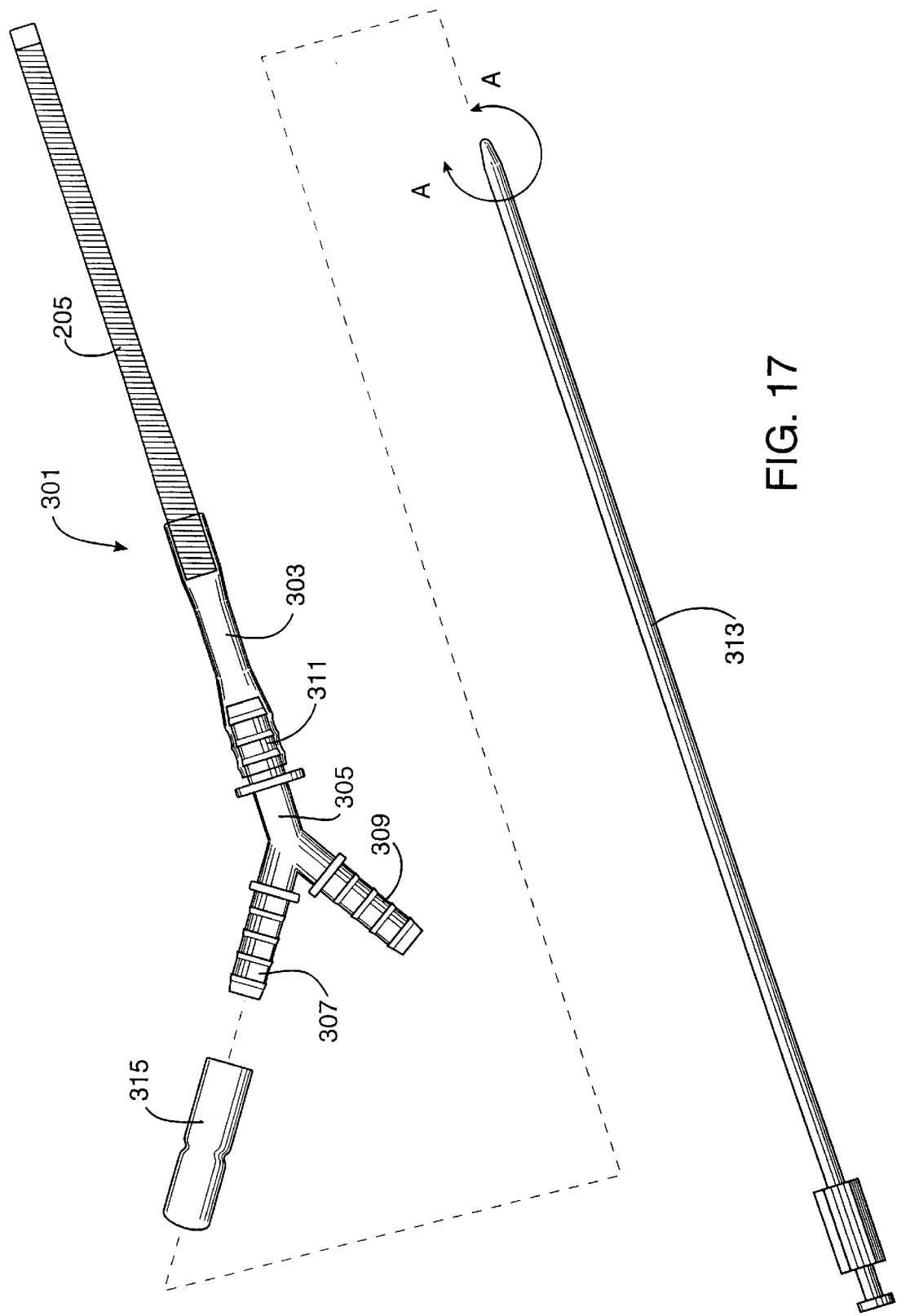
FIG. 17 shows an exploded view of another arterial return cannula.

Referring to FIG. 17, another preferred cannula 301 is shown. The cannula 301 is preferably used as the arterial return cannula for the CPB system described above. The cannula 301 includes the reinforced section 205 as described above. A tube 303 connects the reinforced section 205 to a Y-connector 305 which has first, second and third connections 307, 309, 311. The tube 303 is preferably a flexible tube made of estane 58810 42D polyether polyurethane. When using the cannula 301 for the CPB system described above, the first connection 307 is coupled to a source of oxygenated blood (not shown) while the second connection 309 receives an aortic occlusion catheter (not shown). The aortic occlusion catheter is used to occlude the ascending aorta and deliver cardioplegic fluid for arresting the patient's heart. The second connection 309 preferably receives the extension tube 62 and hemostasis valve 876 for receiving the aortic occlusion catheter in the manner described above in connection with FIGS. 1–4.

Figure 20:
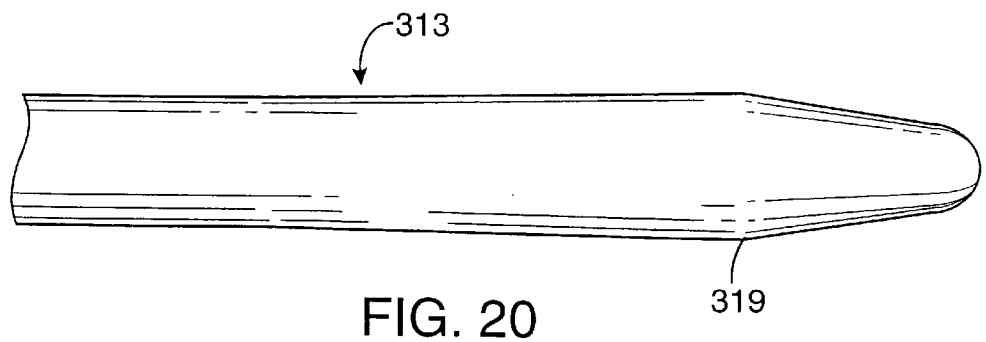
FIG. 20 shows an enlarged view of the distal end of an obturator used with the arterial return cannula of FIG. 17 along line A—A.

A dilator 313 is used to facilitate introduction of the cannula 301 into the patient's artery. A dilator seal 315 seals the space between the cannula 301 and dilator 313. The dilator seal 315 and dilator 313 are removed after the cannula 301 has been introduced into the patient. Referring to FIG. 20, the end of the dilator 313 has an enlarged end 319 which engages an interior wall of the reinforced section 205 when passing through the cannula 301. The enlarged end 319 is preferred so that the dilator 313 does not contact the cannula 301 throughout the length of the dilator 313 thereby reducing the resistance to moving the dilator 313 through the cannula 301.

Figure 18:
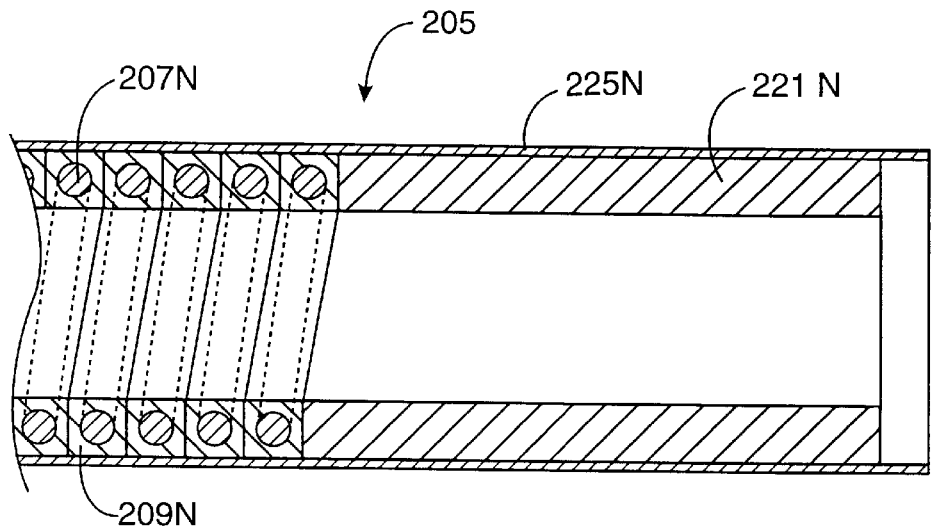
FIG. 18 shows the distal end of the arterial return cannula of FIG. 17 before heating.

Referring to FIG. 18, the method of forming the reinforced section 205 is shown. The reinforced section 205 has an elongate member 207N coated with a coating 209N with the elongate member 207N and coating 209N being any of the members 207A–M and coatings 209A–M described above in connection with FIGS. 6–16. A preferred elongate member 207N is a 0.008 inch stainless steel wire which is coated with 80A durometer polyurethane to a 0.014×0.014 inch cross-section. The elongate member 207N is wrapped around a mandrel (not shown), as described above in connection with FIGS. 6–16, and a soft tip 221N is butted against the elongate member 207N. The soft tip 221N preferably has the same thickness as the coated elongate member 207N with a preferred material being 90A polyurethane.

A layer 225N, which may be the layer 225 described above, is positioned over the coated elongate member 207N and the soft tip 221N. The layer 225N is preferably a tube having a thickness of 0.001–0.005 inch, more preferably about 0.003 inch, and is preferably made of the same material as the soft tip 221N. Although it is preferred to provide the layer 225N over the coated elongate member 207N it is understood that the layer 225N may also be positioned on the radially inner surface of the coated elongate member 207N (or not used at all). When the layer 225N is a tube, the tube has an inner diameter which is slightly smaller than the smallest outer diameter of the reinforced section 205. The tube is positioned over the reinforced section by inflating the tube, inserting the coated elongate member 207N into the tube, and deflating the tube so that the tube contracts around the helically wound coated elongated member 207N. By sizing the layer 225N somewhat smaller than the helically wound elongate member 207N, close contact between the layer 225N and elongate member 207N is ensured.

Figure 19:
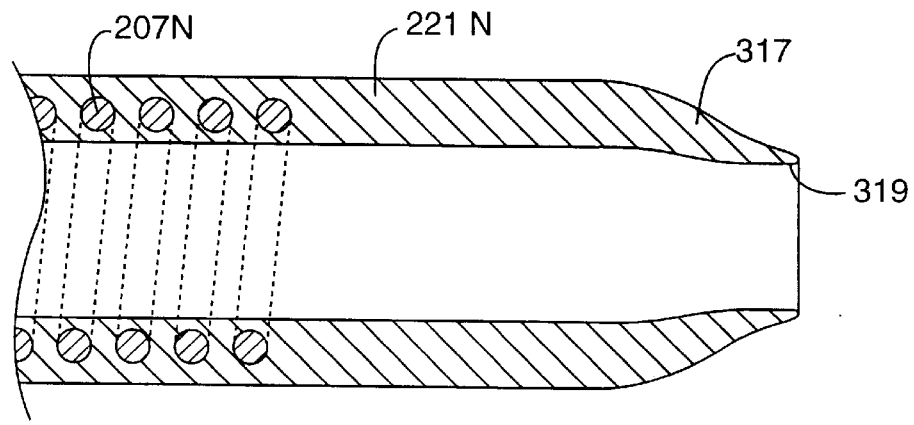
FIG. 19 shows the distal end of the arterial return cannula of FIG. 18 after heating.

A heat shrink tube (not shown) is then positioned over the layer 225N, coated elongate member 207N, and soft tip 221N. The layer 225N, coated elongate member 207N and soft tip 221N are then heated to fuse the material together to form an integral structure as shown in FIG. 19. The tip of the reinforced member 205 is then trimmed and a tapered mandrel is inserted into coated elongate member and a heat shrink tube is recovered over the tip to form a bevel 317 at an end 319 of the soft tip 221N which facilitates atraumatic insertion of the cannula 301. The end 319 is curved inward slightly to form a seal with the dilator 313.

The resulting reinforced section 205 preferably has an internal diameter of at least 0.180 inch, more preferably at least 0.200 inch, more preferably at least 0.236 and most preferably at least 0.242 but no more than 0.375 inch. The reinforced section 205 also preferably has a thickness of no more than 0.0020 inches, more preferably no more than 0.018 inches, and most preferably no more than 0.016 inch. When the coated elongate member 207N has a 0.014×0.014 inch exterior surface and the layer 225N has a 0.003 inch thickness the resulting thickness is about 0.0016 inch since about 0.001 inch is lost when the coated elongate member 207N and layer 225N are compressed with the shrink tube during heating. The unique combination of inner diameter and wall thickness provides an excellent cannula.

The methods and devices disclosed herein have been described in conjunction with cannulas, however, it is understood that the methods and apparatus may also be used for constructing any other hollow tubes including catheters and the like. While the above is a preferred description of the invention, various alternatives, modifications and equivalents may be used without departing from the scope of the invention. For example, the opposing sides of the coated elongate member 207 may have an S-shape, and the reinforced section 205 may have a varying wall thickness. Therefore, the above description should not be taken as limiting the scope of the invention which is defined by the claims.

We claim:

1. A method comprising the steps of:

coating an elongate member with a material thereby forming a coated elongate member, the coated elongate member having opposing sides;

winding the coated elongate member so that the opposing sides are facing one another;

melting the material on the coated elongate member after the winding step so that the opposing sides fuse together to form a reinforced tube having a finite length;

forming a medical device with the reinforced tube, the medical device having a wall thickness equal to or less than 0.018 inch;

inserting at least a portion of the reinforced tube into a patient; and performing a medical procedure on the patient with the medical device after the inserting step.

2. The method of claim 1, further comprising the steps of:

compressing the coated elongate member with a shrink tube after the winding step and before the melting step; and removing the shrink tube after the melting step.

3. The method of claim 1, wherein:

the coating step is carried out by coextruding the material over the elongate member.

4. The method of claim 1, wherein:

the coating step is carried out with the material being a substance selected from the group consisting of thermoplastics.

5. The method of claim 1, wherein:

the coating step is carried out with the material being a material selected from the group consisting of polyurethane, polyether block amide and PVC.

6. The method of claim 1, further comprising the step of:

dipping the coated elongate member in a solution after the winding step.

7. The method of claim 1, wherein:

the coating step is carried out so that the coated elongate member has a polygonal-shaped cross-section.

8. The method of claim 7, wherein:

the coextruding step is carried out so that the polygonal-shaped cross-section is a quadrangle.

9. The method of claim 1, wherein:

the winding step is carried out so that the coated elongate member forms a structure having a circular cross-sectional shape.

10. The method of claim 1, wherein:

the coating step is carried out with the elongate member being a metal wire.

11. The method of claim 1, wherein:

the melting step is carried out by heating the coated elongate member.

12. The method of claim 1, further comprising the step of:

positioning a layer on at least one of a radially inner and a radially outer side of the coated elongate member.

13. The method of claim 1, further comprising the step of:

positioning a tube of material on a radially inner or a radially outer side of the coated elongate member before the melting step;

the melting step being carried out so that the opposing sides fuse together and the material and the tube fuse together to form the reinforced tube.

14. The method of claim 1, wherein:
the forming step is carried out with the medical device having a thickness of 0.014 to 0.017 inch.

15. The method of claim 1, wherein:
the forming step is carried out with the medical device having a lumen having an inner diameter of at least 0.180 inch.

16. The method of claim 1, wherein:
the forming step is carried out with the lumen having an inner diameter of at least 0.236 inch.

17. The method of claim 1, wherein:
the winding step is carried out with adjacent portions of the coated elongate member having a centerline spacing of less than 0.022 inch.

18. A method comprising the steps of:
coating an elongate member with a material thereby forming a coated elongate member, the coated elongate member having opposing sides;
winding the coated elongate member so that the opposing sides are facing one another;
melting the material on the coated elongate member after the winding step so that the opposing sides fuse together to form a reinforced tube having a finite length;
forming a medical device with the reinforced tube;
inserting at least a portion of the reinforced tube into a patient; and
performing a medical procedure on the patient with the medical device after the inserting step;
the winding step being carried out with the coated elongate member forming a structure having a circular cross-sectional shape having a radius which varies along the longitudinal axis.

19. The method of claim 18, wherein:
the forming step is carried out with the medical device having a wall thickness of between 0.014 to 0.017 inch.

20. The method of claim 18, wherein:
the forming step is carried out with the medical device having a wall thickness equal to or less than 0.018 inch.

21. The method of claim 20, wherein:
the forming step is carried out with the medical device having a lumen with an inner diameter of at least 0.180 inch.

22. A method comprising the steps of:
coating an elongate member with a material thereby forming a coated elongate member, the coated elongate member having opposing sides;
winding the coated elongate member so that the opposing sides are facing one another;
positioning a tube on at least one of a radially inner and a radially outer side of the coated elongate member, the layer being a tube having a thickness equal to or less than 0.007 inch;
melting the material and the tube so that the opposing sides fuse together and the material and the tube fuse together to form a reinforced tube having a finite length; and
forming a medical device with the reinforced tube;
inserting at least a portion of the reinforced tube into a patient; and
performing a medical procedure on the patient with the medical device after the inserting step.

23. The method of claim 22, wherein:
the positioning step is carried out with the thickness of the tube being between 0.001 and 0.003 inch.

24. The method of claim 22, wherein:
the forming step is carried out with the medical device having a wall thickness equal to or less than 0.018 inch.

25. The method of claim 24, wherein:
the forming step is carried out with the medical device having a lumen having an inner diameter of at least 0.180 inch.

26. A method comprising the steps of:
coating an elongate member with a material thereby forming a coated elongate member, the coated elongate member having opposing sides;
winding the coated elongate member so that the opposing sides are facing one another;
positioning a shrink tube over the coated elongate member after the winding step, the shrink tube applying a compressive force to the coated elongate member;
melting the coated elongate member after the winding step so that the opposing sides fuse together and form a matrix around the elongate member to form a reinforced tube having a finite length;
removing the shrink tube after the melting step;
forming a medical device with the reinforced tube, the medical device having a wall thickness of between 0.014 and 0.017 inch;
inserting at least a portion of the reinforced tube into a patient; and
performing a medical procedure on the patient with the medical device after the inserting step.

27. The method of claim 26, further comprising the step of:
positioning a layer on at least one of a radially inner and a radially outer side of the coated elongate member.

28. The method of claim 26, wherein:
the winding step is carried out with adjacent portions of the coated elongate member having a centerline spacing equal to or less than 0.022 inch.

29. The method of claim 26, wherein:
the forming step is carried out with the medical device having a lumen having an inner diameter of at least 0.180 inch.

* * * * *